(12) United States Patent
English et al.

(10) Patent No.: US 12,734,365 B2
(45) Date of Patent: Sep. 15, 2026

(54) HEADER INDEX LOCKING BORE ASSEMBLY

(71) Applicant: Cardiac Pacemakers, Inc., St. Paul, MN (US)

(72) Inventors: James Michael English, Cahir (IE); Moira B. Sweeney, St. Paul, MN (US); Robert Allen Jones, Lake Elmo, MN (US); Benjamin J. Haasl, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 243 days.

(21) Appl. No.: 18/390,625

(22) Filed: Dec. 20, 2023

(65) Prior Publication Data

US 2024/0226584 A1 Jul. 11, 2024

Related U.S. Application Data

(60) Provisional application No. 63/438,196, filed on Jan. 10, 2023.

(51) Int. Cl.
*A61N 1/375* (2006.01)

(52) U.S. Cl.
CPC .................................. *A61N 1/3752* (2013.01)

(58) Field of Classification Search
CPC .................................................... A61N 1/3752
See application file for complete search history.

(56) References Cited

U.S. PATENT DOCUMENTS 8,437,855 B2 5/2013 Sjostedt et al.
8,480,437 B2 7/2013 Dilmaghanian et al.
2021/0187306 A1 6/2021 Spadgenske et al.
2022/0047876 A1 2/2022 Becklund et al.
2022/0062647 A1* 3/2022 English ................ A61N 1/3752
2022/0193423 A1* 6/2022 Baqar .................. A61N 1/3752

FOREIGN PATENT DOCUMENTS

WO 2022/140272 A1 6/2022

OTHER PUBLICATIONS

International Preliminary Report on Patentability received for PCT Patent Application No. PCT/US2023/085061, mailed on Jul. 24, 2025, 9 pages.
International Search Report and Written Opinion received for PCT Patent Application No. PCT/US2023/085061, mailed on Apr. 16, 2024, 10 pages.

* cited by examiner

*Primary Examiner* — Tammie K Marlen
(74) *Attorney, Agent, or Firm* — Nelson Mullins Riley & Scarborough LLP

(57) ABSTRACT

An implantable medical device can include a housing including electronic devices within the housing, and a header attached to the housing. The header can have an index locking assembly including one or more connector bores arranged within the header, each of the one or more connector bores including a proximal end and a distal end. The index locking assembly can also include one or more connector pins configured to be inserted into and interference fit within the one or more connector bores. The proximal end of the one or more connector bores and a portion of the one or more connector pins can include a tapered portion configured to prevent rotation of the one or more connector pins when inserted into the one or more connector bores.

20 Claims, 4 Drawing Sheets

100
110
105
10
15
17
114
102
116
118
112
119
119
120
122
5

200
204
204
202
202

300
306
306
304
304
308
302
302
310

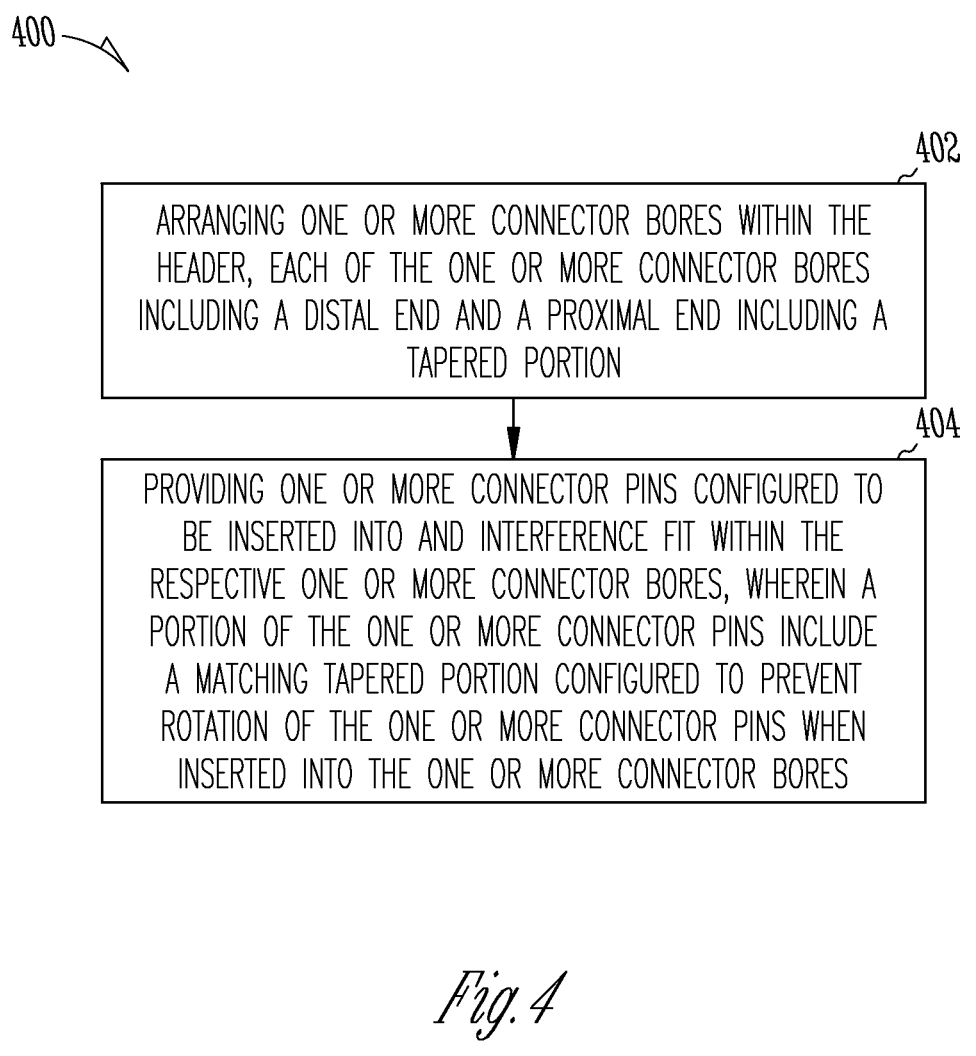

400

402

ARRANGING ONE OR MORE CONNECTOR BORES WITHIN THE HEADER, EACH OF THE ONE OR MORE CONNECTOR BORES INCLUDING A DISTAL END AND A PROXIMAL END INCLUDING A TAPERED PORTION

404

PROVIDING ONE OR MORE CONNECTOR PINS CONFIGURED TO BE INSERTED INTO AND INTERFERENCE FIT WITHIN THE RESPECTIVE ONE OR MORE CONNECTOR BORES, WHEREIN A PORTION OF THE ONE OR MORE CONNECTOR PINS INCLUDE A MATCHING TAPERED PORTION CONFIGURED TO PREVENT ROTATION OF THE ONE OR MORE CONNECTOR PINS WHEN INSERTED INTO THE ONE OR MORE CONNECTOR BORES

*Fig. 4*

HEADER INDEX LOCKING BORE ASSEMBLY

CLAIM OF PRIORITY

This application claims the benefit of U.S. Provisional Application No. 63/438,196, filed on Jan. 10, 2023, which is hereby incorporated by reference in its entirety.

TECHNICAL FIELD

Various embodiments described herein relate to apparatus, systems, and methods associated with headers of implantable medical devices.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead.

In one configuration, IMDs have a header that is coupled to a container that houses much of the electronics of the IMD. The header can be used to couple a conductor of the lead with circuitry within the implantable device. In some examples, one or more connector pins can be used to connect leads to the header. However, the connector pins require secure placement for proper performance of the device.

SUMMARY

Systems and methods are disclosed to provide an index locking assembly for a header of an implantable medical device.

An example (e.g., "Example 1") of subject matter (e.g., a system, a medical device system, etc.) may comprise a header index locking assembly for a medical device. The header index locking assembly may include one or more connector bores arranged within a header, each of the one or more connector bores including a proximal end and a distal end; and one or more connector pins configured to be inserted into and interference fit within the one or more connector bores; wherein the proximal end of the one or more connector bores and a portion of the one or more connector pins have a cylindrical shape including a tapered portion configured to prevent rotation of the one or more connector pins when inserted into the one or more connector bores.

In Example 2, the subject matter of Example 1 may optionally be configured such that the tapered portion includes a taper angle configured to have a predetermined relationship with a coefficient of friction between the one or more connector bores and the one or more connector pins.

In Example 3, the subject matter of any one or more of Examples 1-2 may optionally be configured such that the taper angle is less than five degrees.

In Example 4, the subject matter of any one or more of Examples 1-3 may optionally be configured such that the taper angle is between two and three degrees.

In Example 5, the subject matter of any one or more of Examples 1-4 may optionally be configured such that the one or more connector bores include a plastic material.

In Example 6, the subject matter of any one or more of Examples 1-5 may optionally be configured such that the one or more connector bores include an epoxy material.

In Example 7, the subject matter of any one or more of Examples 1-6 may optionally be configured such that the one or more connector pins include a metallic material.

An example (e.g., "Example 8") of subject matter (e.g., a medical device, an implantable medical device, etc.) may comprise a housing including electronic devices within the housing; and a header attached to the housing, the header having an index locking assembly including: one or more connector bores arranged within the header, each of the one or more connector bores including a proximal end and a distal end; and one or more connector pins configured to be inserted into and interference fit within the one or more connector bores; wherein the proximal end of the one or more connector bores and a portion of the one or more connector pins include a tapered portion configured to prevent rotation of the one or more connector pins when inserted into the one or more connector bores.

In Example 9, the subject matter of Example 8 may optionally be configured such the tapered portion includes a taper angle configured to have a predetermined relationship with a coefficient of friction between the one or more connector bores and the one or more connector pins.

In Example 10, the subject matter of any one or more of Examples 8-9 may optionally be configured such that the taper angle is less than five degrees.

In Example 11, the subject matter of any one or more of Examples 8-10 may optionally be configured such that the taper angle is between two and three degrees.

In Example 12, the subject matter of any one or more of Examples 8-11 may optionally be configured such that the one or more connector bores includes a plastic material or an epoxy material.

In Example 13, the subject matter of any one or more of Examples 8-12 may optionally be configured such that the one or more connector pins include a metallic material.

In Example 14, the subject matter of any one or more of Examples 8-13 may optionally be configured such that the tapered portion includes a taper angle based on a type of material of the one or more connector bores.

An example (e.g., "Example 15") of subject matter (e.g., a method) may comprise arranging one or more connector bores within a header, each of the one or more connector bores including a distal end and a proximal end including a tapered portion; and providing one or more connector pins configured to be inserted into and interference fit within the one or more connector bores, wherein a portion of the one or more connector pins include a matching tapered portion configured to prevent rotation of the one or more connector pins when inserted into the one or more connector bores.

In Example 16, the subject matter of Example 15 may optionally be configured such that the tapered portion includes a taper angle configured to have a predetermined relationship with a coefficient of friction between the one or more connector bores and the one or more connector pins.

In Example 17, the subject matter of any one or more of Examples 15-16 may optionally be configured such that the taper angle is less than five degrees.

In Example 18, the subject matter of any one or more of Examples 15-17 may optionally be configured such that the taper angle is between two and three degrees.

In Example 19, the subject matter of any one or more of Examples 15-18 may optionally be configured such that the one or more connector bores includes a plastic material.

In Example 20, the subject matter of any one or more of Examples 15-19 may optionally be configured such that the one or more connector pins includes a metallic material.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

FIG. 4 shows a method of assembling a header for a medical device, in accordance with one embodiment.

DETAILED DESCRIPTION

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized and structural, logical, and electrical changes may be made.

Figure 1:
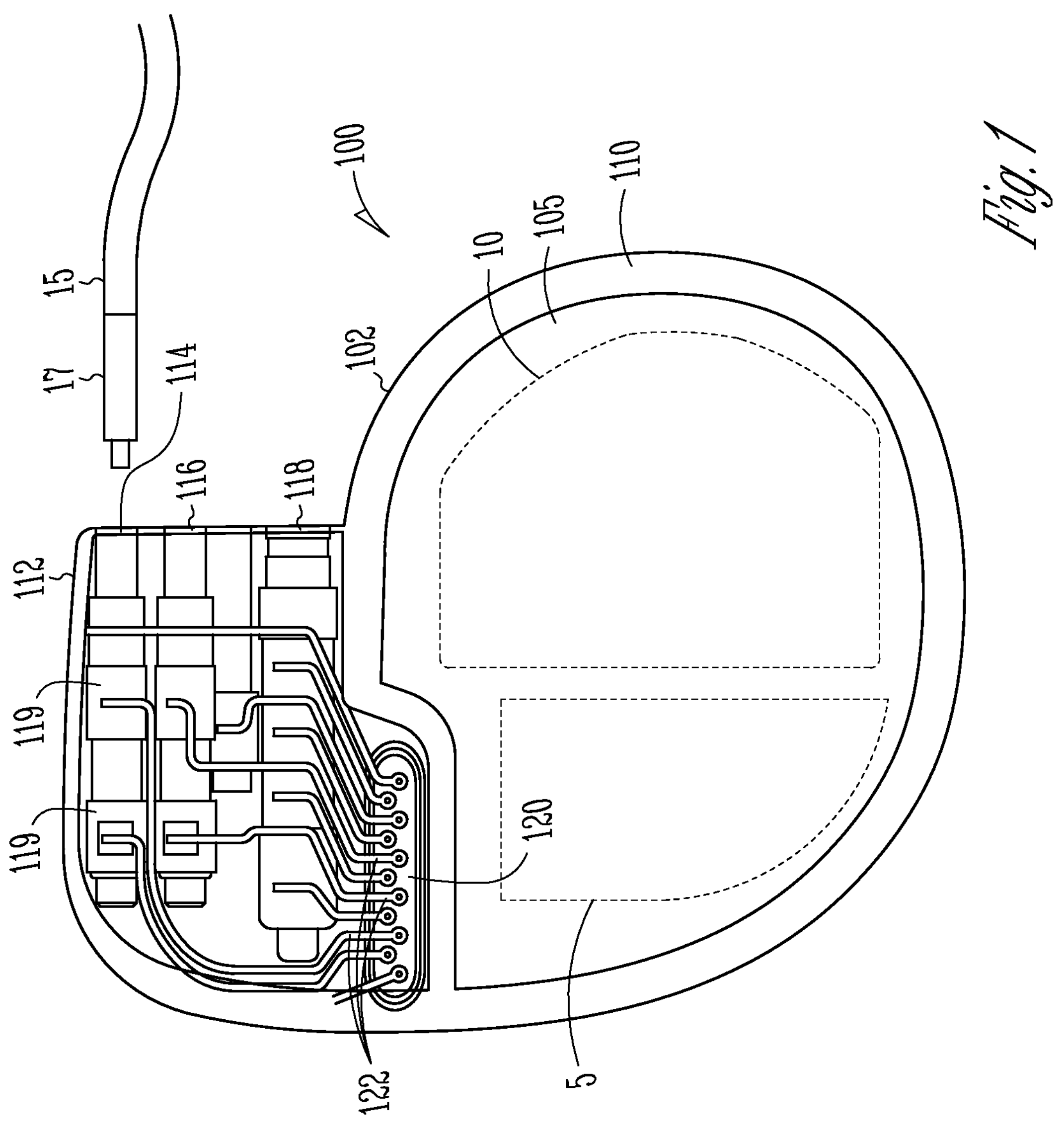
FIG. 1 shows an example implantable medical device, in accordance with one embodiment.

FIG. 1 shows an implantable system 100 including an implantable medical device 102, in accordance with one embodiment. The implantable medical device 102 includes a pulse generator 105 and at least one implantable lead 15. The pulse generator 105 includes a housing 110 and a header 112 mounted to the housing 110. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include electronic devices such as a power supply 5 including a battery, a capacitor, and other components housed in the housing 110. The pulse generator 105 can further include other electronic devices such as microprocessors 10 to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

The header 112 can include one or more bores 114, 116, 118 to receive an implantable lead 15. The implantable lead 15 can include electrodes on a distal end to provide therapy to a body and include a connector pin 17 on the proximal end to couple to the bore 114, 116, 118. At least one electrical conductor is disposed within the lead 15 and extends from the proximal end to the electrode. The electrical conductor carries electrical currents and signals between the pulse generator 105 and the distal electrode.

Contacts on the connector pin 17 can electrically contact electrical contacts 119 within the bores 114, 116, 118 to allow signals and therapy to be delivered to and from the electrodes in a body to the electronics 5, 10 within the housing 110. The contacts 119 can be connected by wires 122 to a feedthrough assembly 120 to electrically communicate between the lead 15 and the electronics within the housing 110.

In one example, the header 112 can be formed from a polymer material. A polymer can provide a number of desirable features, such as biocompatibility, strength, resilience, and ease of manufacturing. In one example, the header 112 is molded separately from the housing 110, and later bonded to the housing 110 using an adhesive. In a second example, the header 112 can be molded in place (overmolded) and contacts a surface of the housing 110 during a curing or hardening process.

In this example, the implantable medical device 102 includes an antenna 130 extending from the housing 110 into the header 112. The antenna 130 can be coupled on one end to a feedthrough assembly 120 attached to the housing 110. The other end of the antenna 130 extends into the header 112.

In other embodiments, the implantable system 100 can also be suitable for use with implantable electrical stimulators, such as, but not limited to, neuro-stimulators, skeletal stimulators, central nervous system stimulators, or stimulators for the treatment of pain.

In this example, the connector pin 17 can be inserted in one of the bores 114, 116, 118. As noted above, during manufacture it is important to control the positioning of the connector pin 17 within the header. The connector pin 17 requires consistent placement for proper performance of the device 102.

Figure 2:
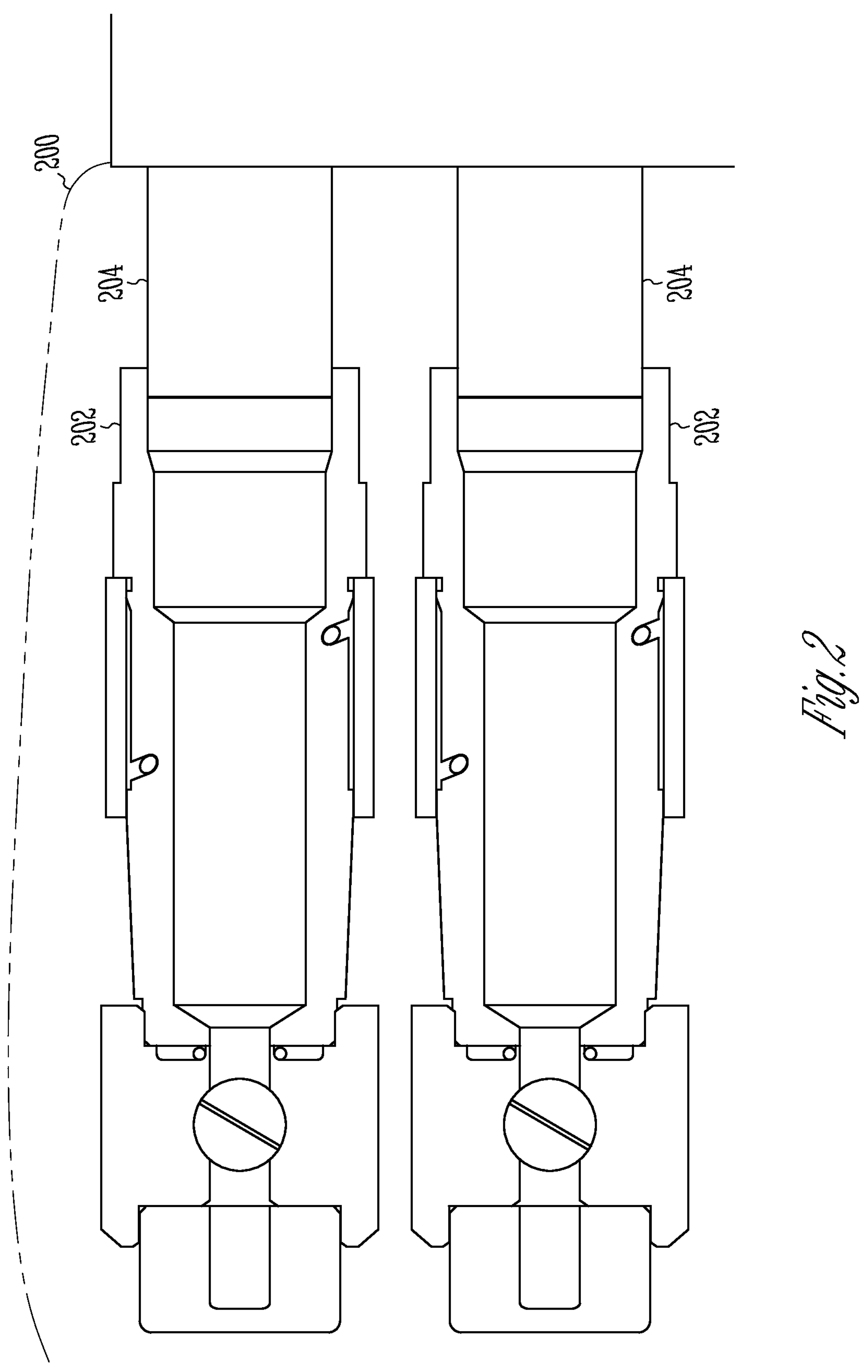
FIG. 2 shows a detail portion of an implantable medical device.
Figure 3:
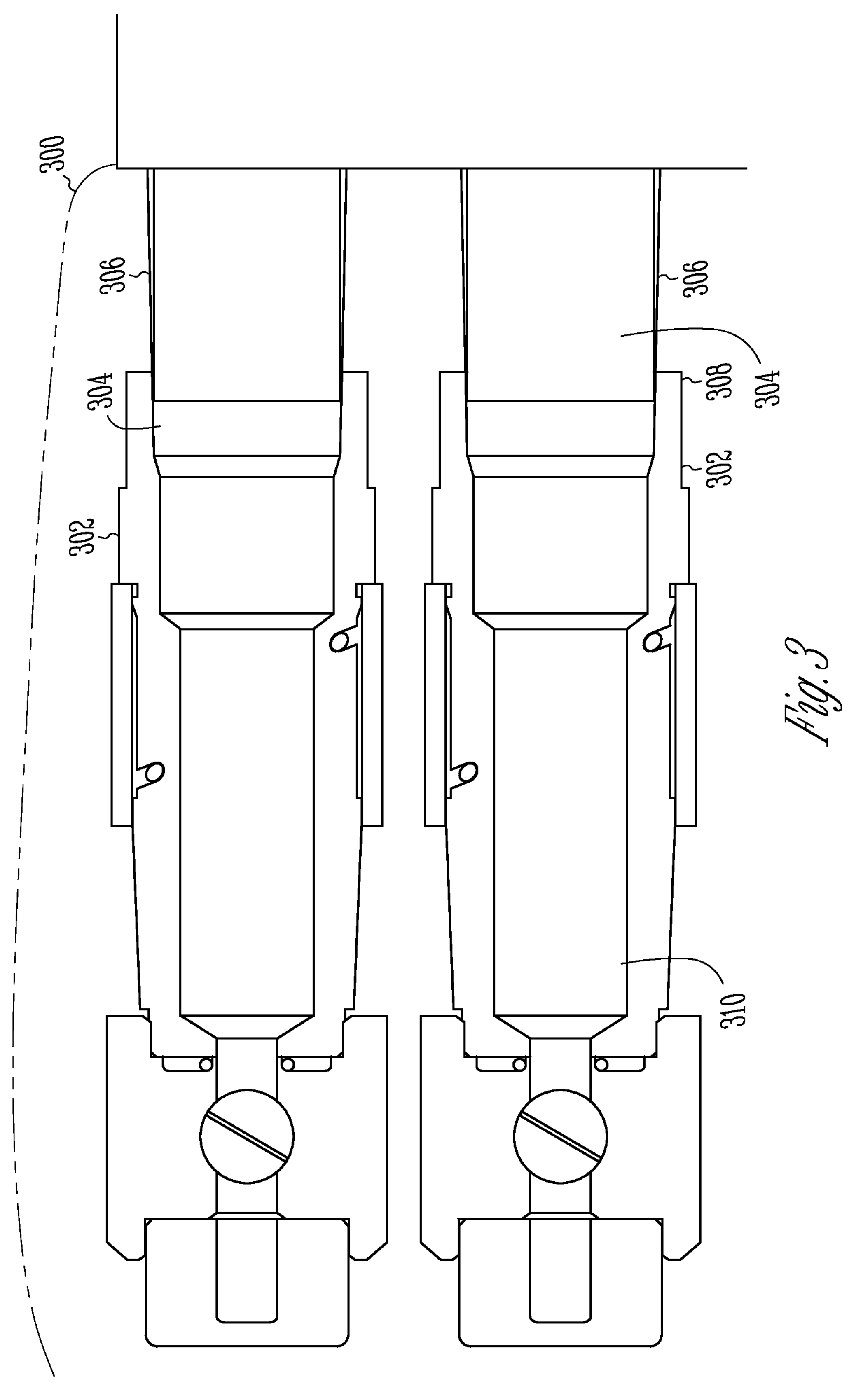
FIG. 3 shows a detail of a portion of the implantable medical device, in accordance with one embodiment.

FIG. 2 shows a detail portion of an implantable medical device. In this view, the device is shown having a header 200 without a tapered portion for the bores 202 and connector pins 204 for sake of reference. FIG. 3 shows a detail of a portion of the implantable medical device, in accordance with one embodiment. In this view, the device is shown having a header 300 with a tapered portion 306 for the bores 302 and connector pins 304.

In various embodiments, the implantable medical device can include a housing including electronic devices within the housing; a header 300 attached to the housing and having an index locking assembly including: one or more connector bores 302 arranged within the header, each of the one or more connector bores 302 including a proximal end 308 and a distal end 310. The device may include one or more connector pins 304 configured to be inserted into and interference fit within the respective one or more connector bores 302, where the proximal end 308 of the one or more connector bores and a portion of the one or more connector pins 304 include a tapered portion 306 configured to prevent rotation of the one or more connector pins 304 when inserted into the one or more connector bores 302.

In various examples, the tapered portion includes a taper angle configured to have a predetermined relationship with a coefficient of friction between the one or more connector bores and the respective one or more connector pins. In one example, the taper angle is less than five degrees. Optionally, the taper angle is between two and three degrees. Other taper angles may be used without departing from the scope of the present subject matter. In some examples, the one or more bores include a plastic material, a metal, or a plastic and a metal. The one or more bores include an epoxy material, in an example. In various examples, the one or more connector pins include a metallic material.

FIG. 4 shows a method of assembling a header index locking assembly for a medical device, in accordance with one embodiment. The method can include arranging one or more connector bores within the header, each of the one or more connector bores including a distal end and a proximal end including a tapered portion, at step 402. At step 404, the method 400 can include providing one or more connector pins configured to be inserted into and interference fit within the respective one or more connector bores, wherein a portion of the one or more connector pins include a matching tapered portion configured to prevent rotation of the one or more connector pins when inserted into the one or more connector bores.

The present device, system and method can provide for manufacturing of header to ensure tolerance and alignment of one or more bores. The present subject matter prevents freedom of the one or more bores to rotate when on connector pins. Previously, the bores were in free space before application of epoxy. The present subject matter provides a taper with an angle range that can be self-locking of the cores to stop cores from rotating during manufacture. Optionally, a pin may be provided before overmolding, or angled sealing ribs can be used. The present subject matter can use a taper section to provide for lower insertion force and improved lead relative motion and seal configuration for the bores of the header, in various examples.

In various examples, the cylindrical portions of the bores and connector pins provide for a press fit or interference fit, and can include surfaces parallel with each other and having a relatively small taper (such as 2 to 3 degrees) to improve friction between surfaces. The taper angle can be selected based on coefficients of friction (such as 10× the coefficient of friction) of the respective surface to help prevent rotation of the pins with respect to the bore. Other levels of friction can be used without departing from the scope of the present subject matter. In some examples, a critical angle under 4 degrees can be used. Other angles of taper may be used without departing from the scope of the present subject matter.

In various examples, the bore can include a cylindrical opening into the header interface. A connector pin can be inserted into the bore, and using a matching taper on the connector pin and bore, including using the taper on both metallic and plastic portions of the bore, can lock the connector pin in place. The taper angled portion can be used on each bore, on each interface on each block and face, and on any plastic interlocking with metal blocks. As used herein, the lead bore entry is considered as part of the bore. In various examples, a header may include one to five or more bores, and the header usually includes two to three bores. The present subject matter can be used with any header that has core with a solid plastic piece, and can be retrofit to existing headers, in various examples. The angle of tapered portion may be varied based on the type of plastic or material of the bore, in various examples. The present subject matter provides for construction of a bore to provide a machined angle of a taper, in various examples. The machined angle can provide for critical interference for any interlocking metal on metal, or plastic on metal, or on a pin that marks lead bore entry, in various examples.

As noted, after the other header components are positioned, the entire header can be overmolded to keep all the components in place. Accordingly, the subject matter of the present disclosure provides for ease of manufacturing because the user does not have to struggle to keep the connector pins within the connector bores. Without the use of the taper angle configured to hold the connector pins within the connector bores, it can be easy for the connector pins to rotate during placement of other components of the header and before the header is overmolded.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A header index locking assembly for a medical device, the header index locking assembly comprising:

one or more connector bores arranged within a header, each of the one or more connector bores including a proximal end and a distal end; and one or more connector pins configured to be inserted into and interference fit within the one or more connector bores;

wherein the proximal end of the one or more connector bores and a portion of the one or more connector pins have a cylindrical shape including a tapered portion configured to prevent rotation of the one or more connector pins when inserted into the one or more connector bores.

2. The header index locking assembly of claim 1, wherein the tapered portion includes a taper angle configured to have a predetermined relationship with a coefficient of friction between the one or more connector bores and the one or more connector pins.

3. The header index locking assembly of claim 2, wherein the taper angle is less than five degrees.

4. The header index locking assembly of claim 2, wherein the taper angle is between two and three degrees.

5. The header index locking assembly of claim 1, wherein the one or more connector bores include a plastic material.

6. The header index locking assembly of claim 1, wherein the one or more connector bores include an epoxy material.

7. The header index locking assembly of claim 1, wherein the one or more connector pins include a metallic material.

8. The header index locking assembly of claim 1, wherein the one or more connector bores extend from a proximal end of the header toward a distal end of the header, and the one or more connector pins extend into the one or more connector bores in a direction from the proximal end toward the distal end.

9. The header index locking assembly of claim 8, wherein the tapered portion is configured to create a self-locking interference fit between the one or more connector bores and the one or more connector pins to prevent rotation of the one or more connector pins when inserted into the one or more connector bores.

10. The header index locking assembly of claim 9, wherein the tapered portion prevents rotation of the one or more connector pins during assembly of the header before application of an epoxy material.

11. An implantable medical device comprising:

a housing including electronic devices within the housing; and a header attached to the housing, the header having an index locking assembly including:

one or more connector bores arranged within the header, each of the one or more connector bores including a proximal end and a distal end; and one or more connector pins configured to be inserted into and interference fit within the one or more connector bores;

wherein the proximal end of the one or more connector bores and a portion of the one or more connector pins include a tapered portion configured to prevent rotation of the one or more connector pins when inserted into the one or more connector bores.

12. The implantable medical device of claim 11, wherein the tapered portion includes a taper angle configured to have a predetermined relationship with a coefficient of friction between the one or more connector bores and the one or more connector pins.

13. The implantable medical device of claim 12, wherein the taper angle is less than five degrees.

14. The implantable medical device of claim 12, wherein the taper angle is between two and three degrees.

15. The implantable medical device of claim 11, wherein the one or more connector bores include a plastic material.

16. The implantable medical device of claim 11, wherein the one or more connector bores include an epoxy material.

17. The implantable medical device of claim 11, wherein the one or more connector pins include a metallic material.

18. A method of assembling a header index locking assembly for a medical device, the method comprising:

arranging one or more connector bores within a header, each of the one or more connector bores including a distal end and a proximal end including a tapered portion; and providing one or more connector pins configured to be inserted into and interference fit within the one or more connector bores, wherein a portion of the one or more connector pins include a matching tapered portion configured to prevent rotation of the one or more connector pins when inserted into the one or more connector bores.

19. The method of claim 18, wherein the tapered portion includes a taper angle configured to have a predetermined relationship with a coefficient of friction between the one or more connector bores and the one or more connector pins, wherein the taper angle is less than five degrees, wherein the one or more connectors bores include a plastic material, wherein the one or more connector pins include a metallic material.

20. The method of claim 19, wherein the taper angle is between two and three degrees.

* * * * *